(12) United States Patent
Restelli et al.

(10) Patent No.: US 10,370,359 B2
(45) Date of Patent: Aug. 6, 2019

(54) PROCESS FOR THE PREPARATION OF CRYSTALLINE DEXLANSOPRAZOLE

(71) Applicant: DIPHARMA FRANCIS S.r.l., Baranzate (IT)

(72) Inventors: Alessandro Restelli, Baranzate (IT); Alessio Bove, Baranzate (IT); Gabriele Razzetti, Baranzate (IT)

(73) Assignee: DIPHARMA FRANCIS S.r.L., Baranzate (MI) (IT)

( * ) Notice: Subject to any disclaimer, the term of this patent is extended or adjusted under 35 U.S.C. 154(b) by 0 days.

(21) Appl. No.: 15/969,383

(22) Filed: May 2, 2018

(65) Prior Publication Data
US 2018/0327383 A1    Nov. 15, 2018

(30) Foreign Application Priority Data

May 9, 2017  (IT) .................. 102017000050223

(51) Int. Cl.
*C07D 401/12* (2006.01)
(52) U.S. Cl.
CPC ........ *C07D 401/12* (2013.01); *C07B 2200/13* (2013.01)
(58) Field of Classification Search
CPC .................................................. C07D 401/12

USPC ......................................................... 546/273.7
See application file for complete search history.

(56) References Cited

U.S. PATENT DOCUMENTS

| 7,285,668 | B2 | 10/2007 | Hashimoto et al. | |
|---|---|---|---|---|
| 8,314,241 | B2 * | 11/2012 | Vladiskovic | C07D 401/12 546/273.7 |
| 8,362,260 | B2 * | 1/2013 | Vladiskovic | C07D 401/12 546/273.7 |
| 2010/0204479 | A1 * | 8/2010 | Vladiskovic | C07D 401/12 546/273.7 |
| 2011/0028728 | A1 | 3/2011 | Vladiskovic et al. | |
| 2013/0197232 | A1 * | 8/2013 | Ray | C07D 401/12 546/273.7 |

FOREIGN PATENT DOCUMENTS

| EP | 2216333 A2 | 8/2010 | |
|---|---|---|---|
| WO | WO 2009/088857 A1 | 7/2009 | |
| WO | WO 2011/004387 A2 | 1/2011 | |
| WO | WO-2012104805 A1 * | 8/2012 | ........... C07D 401/12 |

* cited by examiner

*Primary Examiner* — Daniel R Carcanague
(74) *Attorney, Agent, or Firm* — Sterne, Kessler, Goldstein & Fox P.L.L.C.

(57) ABSTRACT

The present invention relates to a process for the preparation of anhydrous crystalline 2-(R)-[(3-methyl-4-(2,2,2-trifluoroethoxy)-2-pyridinyl)methyl)sulfinyl]-1H-benzimidazole (dexlansoprazole).

15 Claims, 3 Drawing Sheets

PROCESS FOR THE PREPARATION OF CRYSTALLINE DEXLANSOPRAZOLE

CROSS REFERENCE TO RELATED APPLICATIONS

This application claims priority to Italian patent application No. 102017000050223, filed on May 9, 2017, the entirety of which is incorporated herein by reference.

FIELD OF THE INVENTION

The present invention relates to a process for the preparation of anhydrous crystalline 2-(R)-[(3-methyl-4-(2,2,2-trifluoroethoxy)-2-pyridinyl)methyl)sulfinyl]-1H-benzimidazole (dexlansoprazole).

BACKGROUND OF THE INVENTION

Dexlansoprazole, also known as 2-(R)-[(3-methyl-4-(2,2,2-trifluoroethoxy)-2-pyridinyl)methyl)sulfinyl]-1H-benzimidazole, is an enantiomer of lansoprazole. Dexlansoprazole is a proton pump inhibitor and is used in the treatment of pathologies such as erosive esophagitis, gastro-oesophageal reflux disease and gastro-intestinal disorders.

Dexlansoprazole has been disclosed in WO 92/08716 and solid crystalline forms are described in U.S. Pat. No. 6,462,058. U.S. Pat. No. 6,462,058 exemplifies a crystalline anhydrous form (with a melting point of 147-148° C.) and a sesquihydrate form (with a melting point of 76-80° C.).

Crystalline anhydrous Dexlansoprazole, as described in U.S. Pat. No. 7,285,668, has a higher thermal stability than other solid forms of dexlansoprazole. U.S. Pat. No. 7,285,668 also includes processes for obtaining the anhydrous crystalline form by crystallization from $C_1$-$C_4$ alkyl acetate and wherein the compound is dissolved at a concentration of between approximately 0.1 and 0.5 mg/mL. This method for the preparation of crystalline anhydrous dexlansoprazole has a limited industrial applicability, because during said process a significant degradation of the starting products occurs and the yields of crystalline anhydrous dexlansoprazole are low.

U.S. Pat. No. 8,314,241 describes a process for the preparation of crystalline anhydrous dexlansoprazole comprising the dispersion of dexlansoprazole in an alcoholic solvent, its complete dissolution by heating the dispersion of dexlansoprazole at temperatures not higher than 40° C., and the subsequent cooling of the solution to obtain the precipitation of dexlansoprazole in anhydrous crystalline form and the recovery of the solid.

The inventors of the present invention, which are partly the same inventors of U.S. Pat. No. 8,314,241, have surprisingly found a new process for the preparation of crystalline anhydrous dexlansoprazole that differs from the method described in U.S. Pat. No. 8,314,241 and does not include the step of complete dissolution of dexlansoprazole in an alcoholic solvent and the addition of an anti-solvent to precipitate the product. This new method allows for obtaining crystalline anhydrous dexlansoprazole without the formation or increase of degradation products. Furthermore, said crystals have the following advantageous properties: they have a better filterability, they can be more easily formulated, are free of colored impurities, and the crystals are more stable at higher temperatures than those obtained by the method described in U.S. Pat. No. 8,314,241.

SUMMARY AND OBJECT OF THE INVENTION

The present invention is directed to a new process for preparing anhydrous crystalline dexlansoprazole characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, which can be obtained by crystallisation of dexlansoprazole from one or more $C_5$-$C_9$ alkanes or from a mixture comprising one or more $C_5$-$C_9$ alkanes and one or more $C_1$-$C_6$ alcohols.

BRIEF DESCRIPTION OF THE FIGURES AND ANALYTICAL METHODS

The obtained crystalline dexlansoprazole was characterized by X-ray powder diffraction (XRPD) (X-ray powder diffraction) and nuclear magnetic resonance spectrometer ($^1$H-NMR). The water content was determined by titration according to the Karl Fischer technique. The X-ray diffraction spectra (XRPD) were collected with the automatic powder and liquid diffractometer APD-2000 manufactured by Ital-Structures at the following operating conditions: Bragg-Brentano geometry, CuKα radiation (λ=1.5418 Å) scanning from 3 to 40° degrees with 2θ and an angular step time of 0.03° in 1 sec. The $^1$H-NMR spectra were acquired with a Varian Mercury 300 spectrometer and using DMSO-$d_6$ as solvent.

Figure 3:
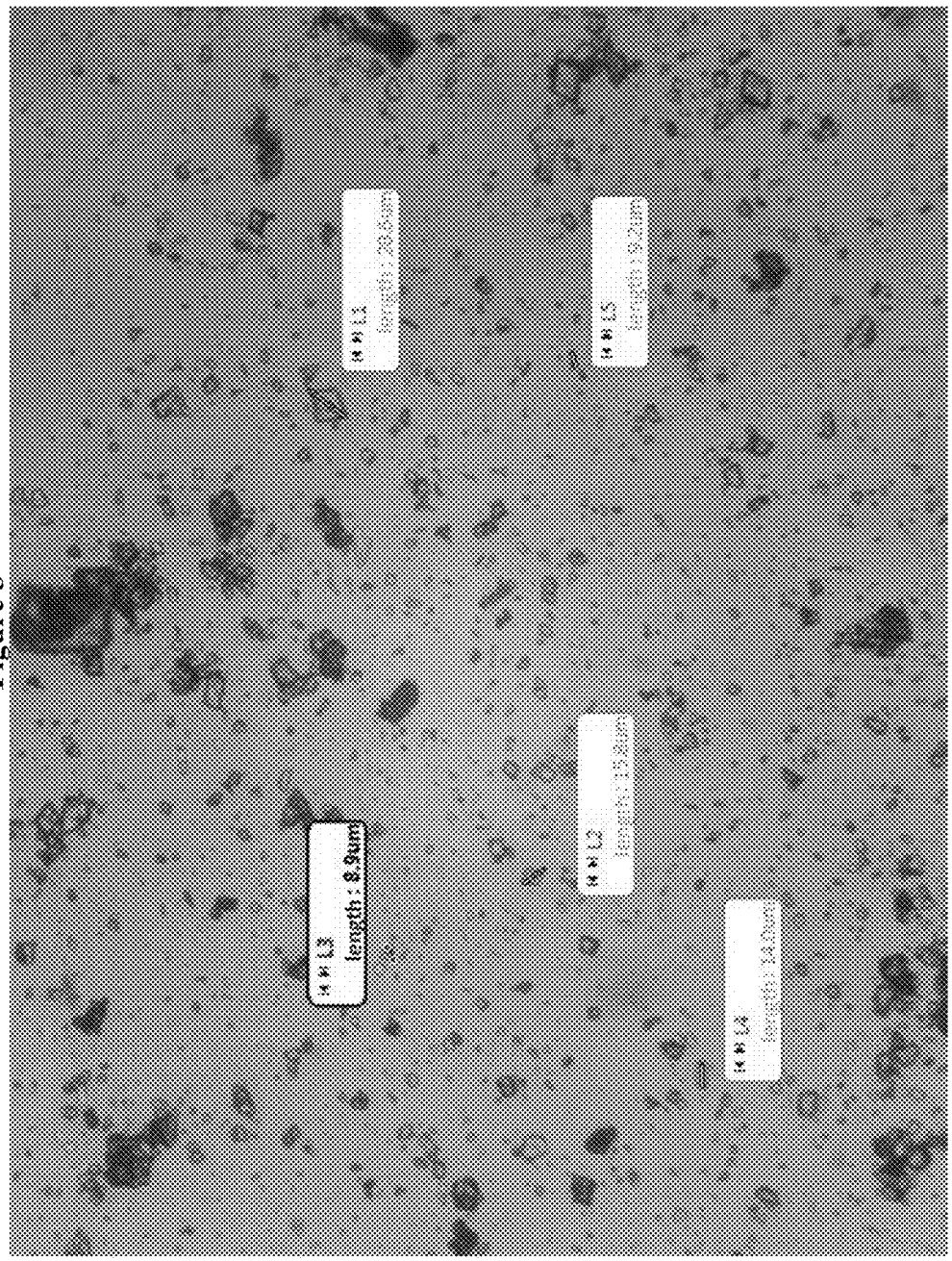

FIG. 3 shows the microscope image of the crystals obtained with the method described in U.S. Pat. No. 8,314,241.

The crystals were analyzed using a Zeiss Axiostar Plus, which is a transmitted light microscope for visualization of fine structures. The microscope is equipped with a binocular tube, an objective magnification of 10× and the size of field of view of 20. Moreover, an A-Plan objective was used for transmitted light with 10× magnification and a numerical aperture of 0.25. The samples were prepared by suspending the product in a 1% solution of tween 20 in water.

DETAILED DESCRIPTION OF THE INVENTION

The present invention relates to a process for the preparation of crystalline anhydrous dexlansoprazole characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, comprising:

a) dispersing dexlansoprazole in one or more $C_5$-$C_9$ alkanes or a mixture comprising one or more $C_5$-$C_9$ alkanes and one or more $C_1$-$C_6$ alcohols at a temperature of up to 50° C. to produce a dispersion;

b) cooling the dispersion to form a precipitate of crystalline anhydrous dexlansoprazole or azeotropically distilling the dispersion at a temperature of up to 50° C. or azeotropically distilling the dispersion at a temperature of up to 50° C. and cooling the dispersion to form a precipitate of crystalline anhydrous dexlansoprazole; and c) recovering the solid.

In another aspect, the present invention relates to a process for the preparation of crystalline anhydrous dexlansoprazole characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, consisting of:

a) dispersing dexlansoprazole in one or more $C_5$-$C_9$ alkanes or a mixture comprising one or more $C_5$-$C_9$ alkanes and one or more $C_1$-$C_6$ alcohols at a temperature of up to 50° C. to produce a dispersion;

b) cooling the dispersion to form a precipitate of crystalline anhydrous dexlansoprazole or azeotropically distilling the dispersion at a temperature of up to 50° C. or azeotropically distilling the dispersion at a temperature of up to 50° C. and cooling the dispersion to form a precipitate of crystalline anhydrous dexlansoprazole; and c) recovering the solid.

One embodiment of the invention relates to a process for the preparation of crystalline anhydrous dexlansoprazole, wherein the most intense peaks are at 7.5, 11.4, 13.1, 13.5, 15.1, 15.4, 17.3, 20.0, 21.7, 22.5, 24.0, 26.1, 27.3 and 28.6±0.2° in 2θ.

In one embodiment of the present invention, the process does not comprise a step wherein an anti-solvent or a mixture of anti-solvents is added to the dispersion.

By "comprising" herein is meant that additional steps can be taken in the processing, which do not substantially change the product produced by the reaction. The term comprising encompasses the terms "consisting of" and "consisting essentially of".

According to the present invention, the term "dispersing" used herein means a partial dissolution. An essential aspect of the present invention is that the dispersion of dexlansoprazole does not lead to a complete dissolution of the dexlansoprazole.

The dexlansoprazole used in the dispersion can be in any form thereof. For example, the starting material can be either solid amorphous or crystalline hydrate dexlansoprazole. For example, crystalline hydrate dexlansoprazole can be dexlansoprazole sesquihydrate or crystalline dexlansoprazole in monohydrate form hemisolvated with ethanol (hereafter called form D), known from U.S. Pat. No. 8,362,260.

The solvent can be one or more $C_5$-$C_9$ alkanes, such as from 1 to 3 alkanes, which can be linear or branched. The $C_5$-$C_9$ alkane can be hexane or heptane.

Alternatively, the solvent can be a mixture comprising one or more, typically two or three, $C_5$-$C_9$ alkanes, such as hexane or heptane, and one or more, typically two or three, $C_1$-$C_6$ alcohols, wherein the $C_1$-$C_6$ alcohol, which can be linear or branched, is preferably a linear or branched $C_1$-$C_4$ alcohol. Examples of alcohols are methanol, ethanol, isopropanol, 1-butanol, 2-butanol, preferably isopropanol.

Typically, the ratio of the alcohol and the $C_5$-$C_9$ alkane in the mixture can be 1:1 (volume:volume, v:v) or lower, preferably between about 1:10 (v:v) and 1:1 (v:v), more preferably between about 1:10 (v:v) and about 3:10 (v:v).

In one embodiment the ratio is 2:11 (v:v).

In another embodiment the ratio is 2:9 (v:v).

In an alternative embodiment the ratio is 1:6 (v:v).

The concentration of dexlansoprazole in the present application, unless defined otherwise, is expressed as the ratio between the weight of dexlansoprazole and weight of the solvent or of the mixture of solvents. The concentration is typically between about 5% and about 50%, for example between about 10% and about 40%.

The temperature of the dispersion of dexlansoprazole in the solvent can be up to 50° C., for example at 45° C. In one embodiment, the temperature is up to 40° C. In another embodiment, the temperature is between 20 and 40° C., for example between 30 to 35° C.

If desired, the dispersion of dexlansoprazole in the solvent can be heated to a temperature of up to 50° C., for example at 45° C. In one embodiment, the dispersion is heated to a temperature of up to 40° C. In another embodiment, the temperature is between 20 to 40° C., for example between 30 to 35° C.

The cooling step, which is performed to precipitate the crystalline anhydrous dexlansoprazole, can be carried out at a temperature equal to or lower than about 20° C. In one embodiment, the temperature is between about 0° C. to about 20° C. In another temperature, the temperature is between about 5° C. and about 10° C. In one embodiment, the dispersion can be cooled slowly, for example at a speed between approximately 0.1 and 0.4° C. per minute.

If desired, in order to facilitate the subsequent crystallization, the dispersion of dexlansoprazole can be subjected to azeotropic distillation of the solvent at reduced pressure and at a temperature up to 50° C., for example at 45° C. or up to 40° C., to concentrate the solution. In one embodiment, the azeotropic distillation of the solvent can be carried out between about 20° C. to about 40° C., for example between about 30° C. and about 35° C. Then, the dispersion can be cooled to obtain the anhydrous crystalline dexlansoprazole as described above.

Alternatively to the cooling of the dispersion, the dispersion can be subjected to an azeotropic distillation of the solvent at reduced pressure and at a temperature up to 50° C., for example at 45° C., to obtain the crystalline anhydrous dexlansoprazole. In one embodiment, the temperature is up to 40° C. In another embodiment, the temperature is between about 20° C. to about 40° C., for example between about 30° C. and about 35° C.

One embodiment of the present invention is that the dispersion of dexlansoprazole and any heating or azeotropic distillation of said dispersion is performed maintaining the temperature up to 40° C.

If desired, adding a previously obtained seed crystal of the desired crystalline form can be added to the dispersion.

The recovery of crystalline anhydrous dexlansoprazole can be carried out by known methods, for example by filtration or centrifugation, preferably by filtration on a Buchner filter.

An anti-solvent is a solvent that causes precipitation when added to a solution in another solvent. The present invention in one embodiment does not use of a step of adding a solvent, used as anti-solvent, as initializer of the crystallization of dexlansoprazole, nor as promoter to increase the content of the crystalline anhydrous dexlansoprazole out of the dispersion mixture.

Crystalline anhydrous dexlansoprazole as obtained according to the herein claimed process has a water content of between about 0% and about 1% in weight, such as between about 0.05% and 0.5% or up to 0.3%, so that it can be defined substantially anhydrous.

Crystalline anhydrous dexlansoprazole as obtained according to the herein claimed process is particularly stable at 70° C. In fact, the concentration of the degradation products increased by less than 0.1% (calculated by Area % HPLC at 285 nm) after keeping the herein obtained crystalline anhydrous dexlansoprazole at 70° C. for 72 hours. The concentration of crystalline anhydrous dexlansoprazole decreased by less than 0.1% (calculated by Area % HPLC at 285 nm) after keeping the herein obtained crystalline dexlansoprazole at 70° C. for 72 hours.

Crystalline anhydrous dexlansoprazole obtained according to the method of the present invention has a purity equal to or higher than 99%, such as equal to or higher than 99.5% or higher than 99.9%.

A further embodiment of the present invention is directed to crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, and characterized in that the concentration of crystalline anhydrous dexlansoprazole, after 72 hours at 70° C., decreases less than 0.1% calculated by Area % HPLC at 285 nm.

A further embodiment of the present invention is directed to crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, comprising an impurity of formula (I)

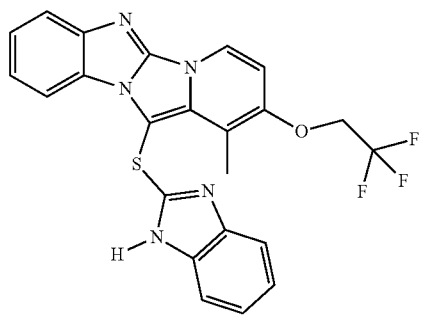

in quantities below 0.1% calculated as HPLC area % (A %) at 285 nm.

In one embodiment of the present invention, crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, comprises an impurity of formula (I)

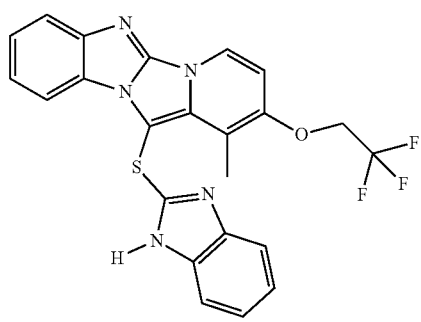

in quantities below 0.05% calculated as HPLC area % (A %) at 285 nm.

In one embodiment of the present invention, crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, comprises an impurity of formula (I)

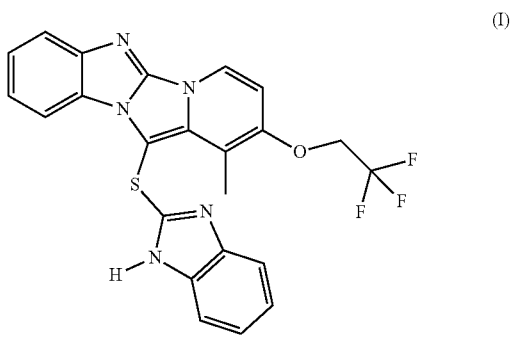 [SMILES: Cc1c(OCC(F)(F)F)ccn2c1c(Sc1nc3ccccc3[nH]1)n1c3ccccc3nc21]

in quantities equal to or lower than 0.03% calculated as HPLC area % (A %) at 285 nm.

A further embodiment of the present invention is directed to a composition, for instance a pharmaceutical composition, comprising crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, in combination with an impurity of formula (I)

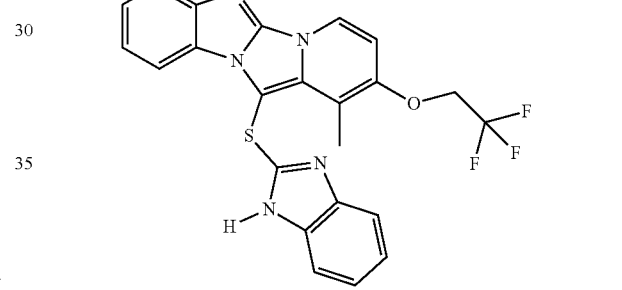

in quantities below 0.1%, calculated as HPLC area % (A %) at 285 nm.

In one embodiment of the present invention, the composition, which can be a pharmaceutical composition, comprises crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, in combination with an impurity of formula (I)

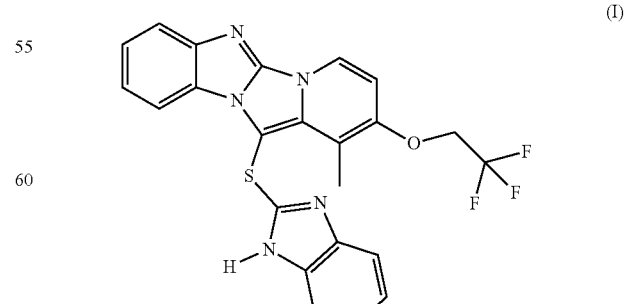

in quantities below 0.05%,
calculated as HPLC area % (A %) at 285 nm.

In one embodiment of the present invention, the composition, which can be a pharmaceutical composition, comprises crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, with a purity equal to or higher than 99%, such as equal to or higher than 99.5% or higher than 99.9%, in combination with an impurity of formula (I)

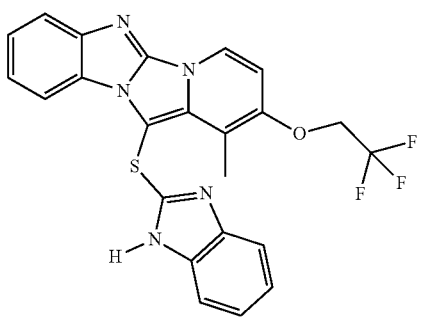

(I)

in quantities equal to or lower than 0.03%,
calculated as HPLC area % (A %) at 285 nm.

The following examples further illustrate the invention.

Example 1. Preparation of Crystalline Anhydrous Dexlansoprazole from Dexlansoprazole Sesquihydrate a) Preparation of Dexlansoprazole Form D 300 g of dexlansoprazole sesquihydrate, which can be prepared according to the procedure described in U.S. Pat. No. 8,198,455, are dissolved in 470 mL of ethanol at about 30° C. and the solution is stirred for about 30-60 minutes until complete dissolution. 1600 mL of an alkane, for example, hexane or heptane, or toluene, are slowly added to the solution and the mixture is then slowly cooled to 0° C. providing dexlansoprazole form D.

b) Preparation of Crystalline Anhydrous Dexlansoprazole

Dexlansoprazole form D, which can optionally be dried under vacuum at room temperature, is then dispersed in 1800 mL of hexane or heptane and the dispersion is heated to approximately 30-35° C. for about 15 minutes to an hour.

Alternatively, the solid dexlansoprazole form D is dispersed in a mixture of 1800 mL of hexane or heptane and 300 mL of isopropanol and the mixture is heated to about 30-35° C. for about 15 minutes to an hour.

Then, the dispersion is concentrated under vacuum, typically by reducing the volume to half the departure and cooled to a temperature lower than 20° C., typically between 5 and 10° C. The mixture is stirred for about an hour, then the solid is filtered off, washed with hexane or heptane and dried in an oven under vacuum at a temperature of about 35° C. providing 242.5 g of crystalline anhydrous dexlansoprazole with a yield of 88%.

Water content: <0.07% (KF).

Figure 1:
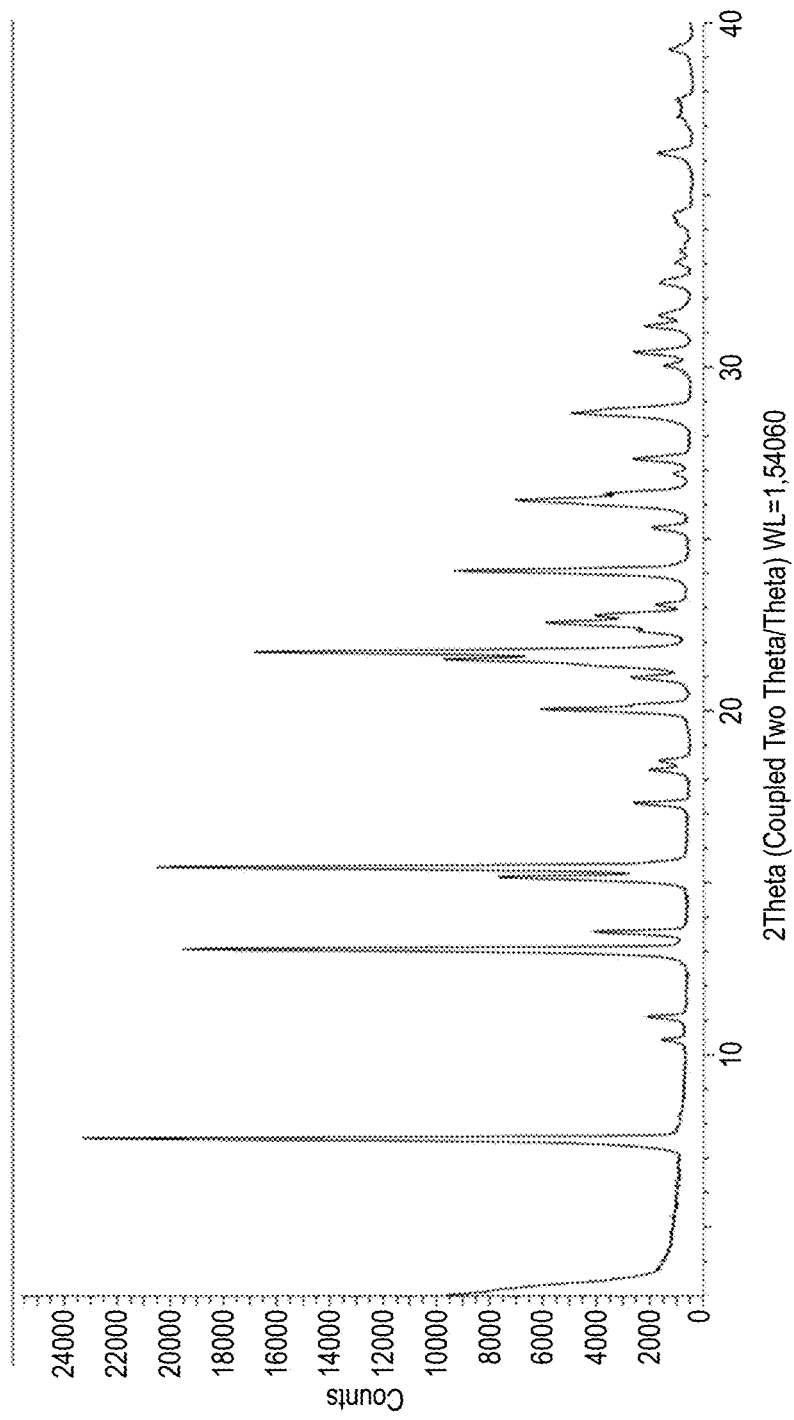
FIG. 1 shows the XRPD spectrum of crystalline anhydrous dexlansoprazole, wherein the most intense peaks are at 7.5, 11.4, 13.1, 13.5, 15.1, 15.4, 17.3, 20.0, 21.7, 22.5, 24.0, 26.1, 27.3 and 28.6±0.2° in 2θ.

The obtained product has an XRPD spectrum as shown in FIG. 1.

$^1$H-NMR (DMSO): d (1H), 8.27 ppm; m (2H), 7.6 ppm; dd (2H), 7.27-7.30 ppm; d (1H), 7.07 ppm; q (2H), 4.84-4.92 ppm; q (2H), 4.72-4.84 ppm; s (3H), 2.16 ppm.

Example 2. Preparation of Crystalline Anhydrous Dexlansoprazole from Dexlansoprazole Sesquihydrate Dexlansoprazole sesquihydrate is dispersed in a $C_5$-$C_9$ alkane, for example hexane or heptane, optionally in the presence of isopropanol, and directly converted into crystalline anhydrous dexlansoprazole according to the same conditions for conversion of dexlansoprazole form D into crystalline anhydrous dexlansoprazole (as described in Example 1).

The obtained product has the XRPD spectrum as shown in FIG. 1 and the $^1$H-NMR spectrum as reported in Example 1.

Example 3. Preparation of Crystalline Anhydrous Dexlansoprazole from Amorphous Dexlansoprazole Amorphous Dexlansoprazole, which can be prepared as described in U.S. Pat. No. 8,362,260, can be converted into crystalline anhydrous dexlansoprazole according to the procedures described in Examples 1 or 2.

The obtained product has the XRPD spectrum as shown in FIG. 1 and the $^1$H-NMR spectrum as reported in Example 1.

Example 4. Preparation of Crystalline Anhydrous Dexlansoprazole from Dexlansoprazole Sesquihydrate (Process of Example 2 of U.S. Pat. No. 8,314,241)

50.1 g of dexlansoprazole sesquihydrate are mixed with 200 ml of 2-butanol and the mixture is heated to 35° C. up to complete dissolution. The mixture is then cooled down to 20° C. at a rate of 0.3° C./min. Optionally, a seed of anhydrous crystalline dexlansoprazole can be added. 400 ml of heptane are slowly added, the mixture is then cooled slowly down to 0° C. and the solid is then isolated by filtration.

The obtained product has the XRPD spectrum as shown in FIG. 1 and the $^1$H-NMR spectrum as reported in Example 1.

Example 5. Preparation of Crystalline Anhydrous Dexlansoprazole from Dexlansoprazole Form D The dispersion of dexlansoprazole form D in a mixture of isopropanol and hexane or heptane in a ratio 2:9 (v:v), instead of 1:6 (v:v), can be converted into the crystalline anhydrous dexlansoprazole following the procedure of Example 1 with a yield of 85%.

The obtained product has the XRPD spectrum as shown in FIG. 1 and the $^1$H-NMR spectrum as reported in Example 1.

Example 6. Preparation of Crystalline Anhydrous Dexlansoprazole from Dexlansoprazole Form D The dispersion of dexlansoprazole form D in a mixture of isopropanol and hexane or heptane in a ratio of 2:11 (v:v), instead of 1:6 (v:v), can be converted into the crystalline anhydrous dexlansoprazole following the procedure of Example 1 with a yield exceeding 79%.

The obtained product has the XRPD spectrum as shown in FIG. 1 and the $^1$H-NMR spectrum as reported in Example 1.

Example 7. Determination of the Stability of Crystalline Anhydrous Dexlansoprazole Prepared According to the Process of the Present Invention in Comparison with the Method of U.S. Pat. No. 8,314,241

The samples of crystalline anhydrous dexlansoprazole prepared according to the method of the present invention (new method) and those made according to the method of U.S. Pat. No. 8,314,241 (present Example 4) are heated in an oven at 70° C.

After 24, 48 and 72 hours, samples are taken and analyzed by HPLC at a wavelength of 285 nm. The percentages [%] of the purity of the samples after 24, 48 and 72 hours at 70° C. are summarized in the following Table 1.

TABLE

| Method | 0 h [%] | 24 h [%] | 48 h [%] | 72 h [%] |
|---|---|---|---|---|
| U.S. Pat. No. 8,314,241 | 99.51 | 99.28 | 99.09 | 98.91 |
| Method of the present invention | 99.96 | 99.95 | 99.93 | 99.93 |

As shown in the table, crystalline anhydrous dexlansoprazole prepared according to the process of the present invention proves to be more stable than that obtained with the method described in U.S. Pat. No. 8,314,241. In fact, crystalline anhydrous dexlansoprazole prepared with the procedure of the present invention virtually does not show any degradation even after 72 hours at 70° C.: the purity of product of 99.93% after 72 is practically identical to the one at time 0 (99.96%). On the other hand, the contents of all the impurities in the product prepared by the method described in U.S. Pat. No. 8,314,241 increases by more than 0.2% after 24 hours, becoming 0.60% after 72 hours.

Figure 2:
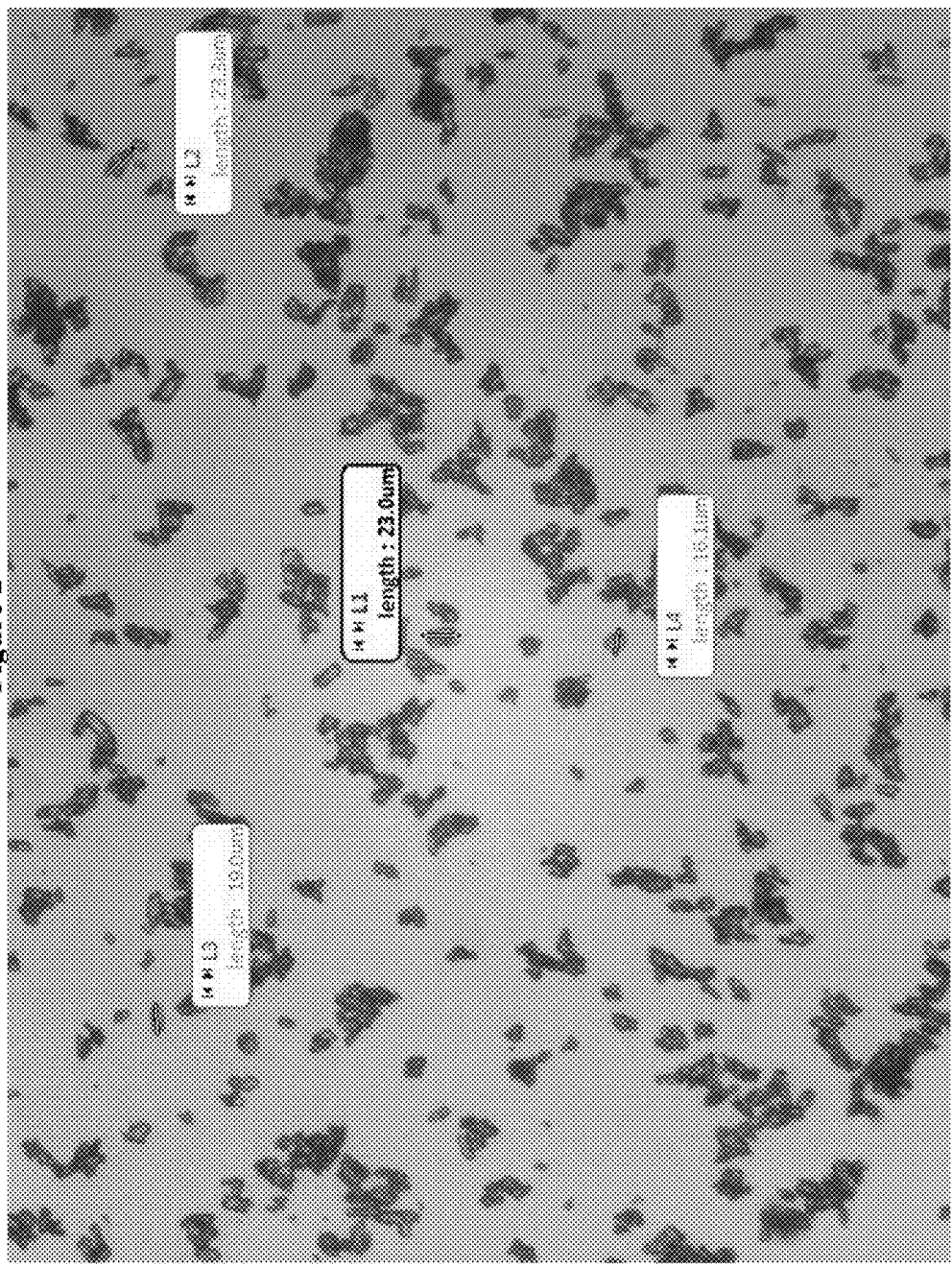
FIG. 2 shows the microscope image of the crystals obtained with the method of the present invention.

The crystals obtained with the two methods result also different inspected under the microscope. As shown in FIGS. 2 and 3, the crystals obtained with the process of the present invention are more homogeneous than those obtained with the method reported in U.S. Pat. No. 8,314,241. In addition, the crystals obtained with the method described in U.S. Pat. No. 8,314,241 are generally smaller (FIG. 3).

The crystals of the present invention are more stable, and can be filtered and formulated more easily. Moreover, contrary to the product obtained according to the method described in U.S. Pat. No. 8,314,241, the crystals prepared according to the herein claimed process do not comprise colored impurities.

Example 8. Determination of the Thermal Stability of Dexlansoprazole in Solution In order to establish the thermal stability of dexlansoprazole the dispersion of dexlansoprazole was heated for 14 hours at 45° C., then a distillation at 50° C. at reduced pressure was performed and finally the dispersion was kept for further 14 hours at 45° C.

The color of the resulting dispersion turned into a slight yellow. HPLC analysis showed that the product complied with the purity specifications required by the FDA (impurity content <0.1%, "Q3B_R2_Guideline" disclosed by the FDA). However, HPLC analysis revealed the formation of the following impurity of formula (I), not present at time 0 and which content reached 0.03% after the termal stress test.

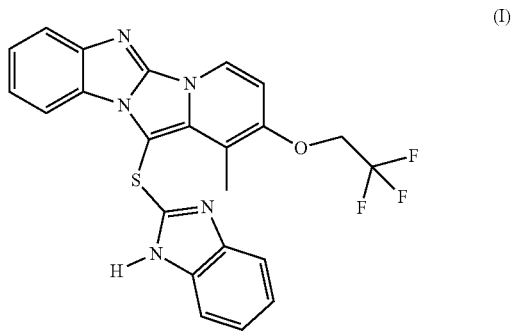 [SMILES: Cc1c(OCC(F)(F)F)ccn2c1c(Sc1nc3ccccc3[nH]1)n1c3ccccc3nc21]

The amount of impurity of formula (I) of yellowish color and already known as an impurity formed due to thermal degradation of dexlansoprazole, increases at higher temperatures. Thus at higher temperatures, the compliance with the purity requirements may be compromised.

The invention claimed is:

1. A process for the preparation of crystalline anhydrous dexlansoprazole, characterized by an XRPD pattern having peaks at 7.5, 11.4, 13.1, 13.5, 15.1, 15.4, 17.3, 20.0, 21.7, 22.5, 24.0, 26.1, 27.3 and 28.6±0.2° in 2θ, comprising:
    a) dispersing dexlansoprazole in one or more $C_5$-$C_9$ alkanes or a mixture comprising one or more $C_5$-$C_9$ alkanes and one or more $C_1$-$C_6$ alcohols at a temperature of up to 50° C. to produce a dispersion;
    b) cooling the dispersion to form a precipitate of crystalline anhydrous dexlansoprazole or
    azeotropically distilling the dispersion at a temperature of up to 50° C. or
    azeotropically distilling the dispersion at a temperature of up to 50° C. and cooling the dispersion to form a precipitate of crystalline anhydrous dexlansoprazole;
    c) recovering the solid; and
    wherein the process does not comprise the step of complete dissolution of dexlansoprazole in an alcoholic solvent.

2. The process according to claim 1, wherein the process does not comprise a step wherein an anti-solvent or mixture of anti-solvents is added to the dispersion.

3. The process according to claim 1, wherein the dexlansoprazole dispersed in step a) is amorphous or crystalline hydrate dexlansoprazole.

4. The process according to claim 3, wherein the crystalline hydrate dexlansoprazole is selected from the group consisting of dexlansoprazole sesquihydrate and crystalline dexlansoprazole monohydrate hemisolvated with ethanol (form D).

5. The process according to claim 1, wherein the $C_5$-$C_9$ alkane is selected from the group consisting of hexane and heptane and wherein the $C_1$-$C_6$ alcohol is selected from the group consisting of methanol, ethanol, isopropanol, 1-butanol and 2-butanol.

6. The process according to claim 1, wherein the ratio between the $C_1$-$C_6$ alcohol and the $C_5$-$C_9$ alkane in the mixture is 1:1 (volume:volume, v:v) or lower.

7. The process according to claim 6, wherein the ratio between the $C_1$-$C_6$ alcohol and the $C_5$-$C_9$ alkane in the mixture is between 1:10 (v:v) and 1:1 (v:v).

8. The process according to claim 7, wherein the ratio between the $C_1$-$C_6$ alcohol and the $C_5$-$C_9$ alkane in the mixture is 2:11 (v:v).

9. The process according to claim 7, wherein the ratio between the $C_1$-$C_6$ alcohol and the $C_5$-$C_9$ alkane in the mixture is 2:9 (v:v).

10. The process according to claim 7, wherein the ratio between the $C_1$-$C_6$ alcohol and the $C_5$-$C_9$ alkane in the mixture is 1:6 (v:v).

11. The process according to claim 1, wherein the concentration of dexlansoprazole in the dispersion is between 5% and 50%.

12. The process according to claim 1, wherein the concentration of dexlansoprazole in the dispersion is between 10% and 40%.

13. The process according to claim 1, wherein the dispersing of dexlansoprazole in the solvent is carried out at a temperature of up to about 40° C.

14. The process according to claim 1, wherein the cooling of the dispersion to form a precipitate of crystalline anhydrous dexlansoprazole is carried out at a temperature lower than or equal to about 20° C.

15. The process according to claim 14, wherein, before the cooling, the dispersion is subjected to azeotropic distillation.

\* \* \* \* \*